United States Patent [19]

Anzai et al.

[11] Patent Number: 4,612,558

[45] Date of Patent: Sep. 16, 1986

[54] FLUORAN COMPOUNDS

[75] Inventors: Mitsutoshi Anzai, Tokyo; Masahiko Yamaguchi, Matsudo; Kazuyuki Wakasugi, Yokohama; Susumu Suzuka, Yono; Michihiro Gonda, Kitamoto; Toshiyuki Abe, Tokyo; Katsumasa Kikkawa, Tokyo; Mikiko Kanasugi, Tokyo, all of Japan

[73] Assignee: Hodogaya Chemical Co., Ltd., Tokyo, Japan

[21] Appl. No.: 710,991

[22] Filed: Mar. 12, 1985

[30] Foreign Application Priority Data

Mar. 24, 1984 [JP] Japan .................................. 59-55285
Apr. 3, 1984 [JP] Japan .................................. 59-65095
Apr. 3, 1984 [JP] Japan .................................. 59-65096

[51] Int. Cl.4 ..................... B41M 5/18; C07D 311/96
[52] U.S. Cl. .................................. 346/221; 427/151; 549/224; 549/225
[58] Field of Search ............... 549/224, 225; 346/221; 427/151

[56] References Cited

U.S. PATENT DOCUMENTS 3,901,918  8/1975  Koga et al. ......................... 549/224
4,226,912 10/1980 Iwasaki et al. ..................... 546/221

FOREIGN PATENT DOCUMENTS 57-116685 7/1982 Japan .
57-144787 9/1982 Japan .

Primary Examiner—Veronica P. Hoke
Attorney, Agent, or Firm—Oblon, Fisher, Spivak, McClelland & Maier

[57] ABSTRACT

A fluoran compound having the formula:

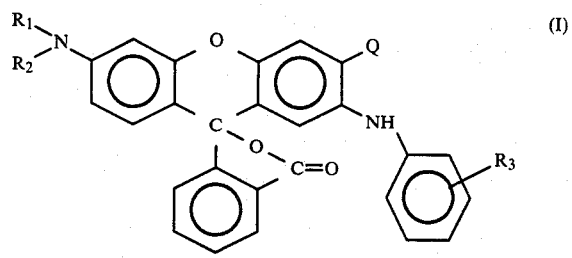

wherein each of $R_1$ and $R_2$ is a hydrogen atom, a straight chain or branched alkyl group having from 1 to 8 carbon atoms, a cyclohexyl group, a substituted or unsubstituted phenyl group, or a substituted or unsubstituted benzyl group, Q is

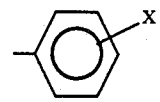

(wherein X is a hydrogen atom, a halogen atom, or a straight chain or branched alkyl group having from 1 to 8 carbon atoms),

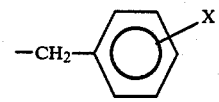

(wherein X is as defined above), or —$(CH_2)_nOR_4$ (wherein $R_4$ is a straight chain or branched alkyl group having from 1 to 8 carbon atoms, a cycloalkyl group, a substituted or unsubstituted phenyl group, or a substituted or unsubstituted benzyl group, and n is an integer of from 1 to 8), and $R_3$ is a hydrogen atom, a halogen atom, a lower fluoroalkyl group, an acyl group, an alkoxy group, an alkoxyalkyl group, or a straight chain or branched alkyl group having from 1 to 8 carbon atoms.

5 Claims, No Drawings

FLUORAN COMPOUNDS

The present invention relates to novel fluoran compounds. More particularly, the present invention relates to novel fluoran compounds having an alkoxy alkyl group, a phenyl group or a benzyl group at the 3-position, which are useful as color precursors for heat sensitive record sheets, electrical heat sensitive record sheets or photo sensitive color-forming record sheets.

Conventional fluoran compounds are disclosed in Japanese Examined Patent Publications Nos. 23204/1976, 29180/1976 and 52759/1981 and Japanese Unexamined Patent Publication No. 16290/1981. The fluoran compounds disclosed in these publications are useful as color formers (color precursors) for heat sensitive record sheets, electrical heat sensitive record sheets or pressure sensitive record sheets. However, heat sensitive record sheets wherein these fluoran compounds are used as color formers, have a drawback that a high temperature is required to obtain a developed color density of 1.0, i.e. energy consumption is high to obtain a developed color density of practical level. Further, they have drawbacks in the humidity decolorization resistance, the oil resistance or the fogging resistance.

The present inventors have conducted extensive researches to overcome the above drawbacks, and as a result, have found that novel fluoran compounds represented by the formula I are colorless or slightly colored solids which are stable in air and which, when brought in contact with an acidic substance, form a dark black color, and that the properties of a heat sensitive record sheets can be remarkably improved by using these compounds.

Namely, the present invention provides a fluoran compound having the formula:

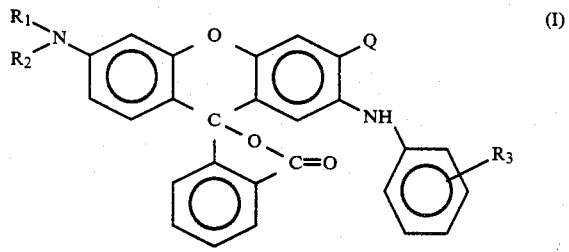
(I)

wherein each of $R_1$ and $R_2$ is a hydrogen atom, a straight chain or branched alkyl group having from 1 to 8 carbon atoms, a cyclohexyl group, a substituted or unsubstituted phenyl group, or a substituted or unsubstituted benzyl group, Q is

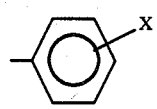

(wherein X is a hydrogen atom, a halogen atom, or a straight chain or branched alkyl group having from 1 to 8 carbon atoms),

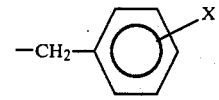

(wherein X is as defined above), or $-(CH_2)_nOR_4$ (wherein $R_4$ is a straight chain or branched alkyl group having from 1 to 8 carbon atoms, a cycloalkyl group, a substituted or unsubstituted phenyl group, or a substituted or unsubstituted benzyl group, and n is an integer of from 1 to 8), and $R_3$ is a hydrogen atom, a halogen atom, a lower fluoroalkyl group, an acyl group, an alkoxy group, an alkoxyalkyl group, or a straight chain or branched alkyl group having from 1 to 8 carbon atoms.

The novel fluoran compounds of the formula I of the present invention are produced by a process which comprises reacting a diphenylamine derivative having the formula:

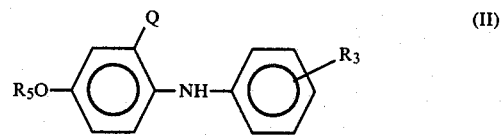
(II)

wherein Q and $R_3$ are as defined above, and $R_5$ is a hydrogen atom, an acetyl group, or a lower alkyl group, with a benzophenone derivative having the formula:

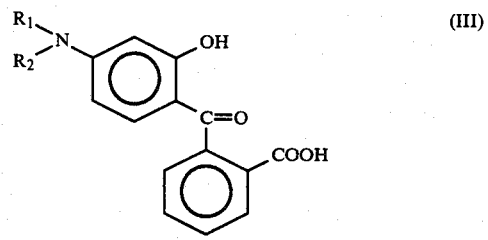
(III)

wherein $R_1$ and $R_2$ are as defined above.

Now, the present invention will be described in detail with reference to the preferred embodiments.

The reaction of the diphenylamine derivative of the formula II with the benzophenone derivative of the formula III is conducted usually in the presence of 80–100% sulfuric acid at a temperature of from 0° to 80° C. for several hours. After the reaction, the reaction mixture is poured into water, and sodium hydroxide is then added to bring the pH to a level of from 8 to 10, whereupon the precipitates are collected by filtration. To the cake, thereby obtained, toluene and an aqueous solution containing from 5 to 10% of sodium hydroxide, are added, and the mixture is stirred for from 1 to 3 hours under reflux, whereupon the toluene layer is separated by liquid separation, washed with water and then concentrated. The precipitated crystals are collected by filtration. The crystals are then dried, whereby a slightly colored novel fluoran compound of the formula I is obtainable in high purity and high yield. If necessary, the product is recrystallized from a volatile organic solvent such as toluene, acetone, butyl acetate or hexane.

As the condensing agent to be used in the present invention, there may be mentioned concentrated sulfuric acid, acetic acid anhydride, phosphoric acid, polyphosphoric acid, phosphorus oxychloride and zinc chloride. From the practical point of view, it is preferred to use 80–100% sulfuric acid which serves as a solvent for a benzophenone compound of the formula III and at the same time serves as a condensing agent.

Now, typical examples of the fluoran compounds of the formula I of the present invention will be given in the following Table. The color hue is a hue of the color developed on a thin layer of silica gel.

TABLE (IV) structure: fluoran with $R_1R_2N-$ on one aromatic ring, $-(CH_2)_nOR_4$ and $-NH-C_6H_4-R_3$ substituents.

| Compound No. | $R_1$ | $R_2$ | $R_3$ | $R_4$ | n | Color Hue |
|---|---|---|---|---|---|---|
| 1 | $-C_2H_5$ | $-C_2H_5$ | H | $-C_2H_5$ | 2 | Reddish black |
| 2 | $-C_4H_9$ | $-C_4H_9$ | " | " | " | Reddish black |
| 3 | cyclohexyl-H | $-CH_3$ | " | " | " | Reddish black |
| 4 | $-C_2H_5$ | $-C_2H_5$ | " | " | 1 | Reddish black |
| 5 | $-C_4H_9$ | $-C_4H_9$ | " | " | " | Reddish black |
| 6 | cyclohexyl-H | $-CH_3$ | " | " | " | Reddish black |
| 7 | " | " | " | $-CH(CH_3)_2$ | " | Reddish black |
| 8 | $-CH_2-C_6H_5$ | " | " | $-C_8H_{17}$ | 2 | Reddish black |
| 9 | $-C_2H_5$ | $-C_2H_5$ | " | $-C_4H_9$ | 4 | Reddish black |
| 10 | " | $-CH_3$ | " | cyclohexyl-H | 2 | Reddish black |
| 11 | phenyl | $-CH(CH_3)_2$ | " | $-C_4H_9$ | 3 | Reddish black |
| 12 | phenyl | $-CH(CH_3)_2$ | 2-Cl | $-C_4H_9$ | " | Reddish black |
| 13 | cyclohexyl-H | $-CH_3$ | " | $-C_2H_5$ | 2 | Reddish black |
| 14 | $-C_4H_9$ | $-C_4H_9$ | 2-Cl | $-C_2H_5$ | 1 | Reddish |

TABLE-continued

| | | | | | |
|---|---|---|---|---|---|
| | | | | | black |
| 15 | cyclohexyl | H | 2-F | cyclohexyl | 4 Reddish black |
| 16 | $-CH_2-C_6H_4-Cl$ | " | " | $-C_2H_5$ | 2 Reddish black |
| 17 | $-C_2H_5$ | $-C_2H_5$ | 4-$CH_2OC_2H_5$ | " | " Reddish black |
| 18 | cyclohexyl | " | 4-$CH_3$ | $-CH_3$ | " Reddish black |
| 19 | $-C_8H_{17}$ | $-CH_3$ | 2-$CF_3$ | $-CH(CH_3)_2$ | " Reddish black |
| 20 | $-C_6H_{13}$ | " | H | $-CH_2-C_6H_5$ | " Reddish black |
| 21 | $-C_2H_5$ | $-C_2H_5$ | H | $-C_6H_5$ | " Reddish black |
| 22 | $-C_2H_5$ | $-i-C_5H_{11}$ | H | $-C_2H_5$ | " Reddish black |
| 23 | $-C_2H_5$ | $-C_2H_5$ | H | $-CH_3$ | 1 Reddish black |
| 24 | $-C_2H_5$ | $-C_2H_5$ | H | $n-C_3H_7$ | " Reddish black |
| 25 | $-C_4H_9$ | $-C_4H_9$ | H | $-CH_3$ | " Reddish black |
| 26 | $-C_4H_9$ | $-C_4H_9$ | H | $-C_4H_9$ | " Reddish black |

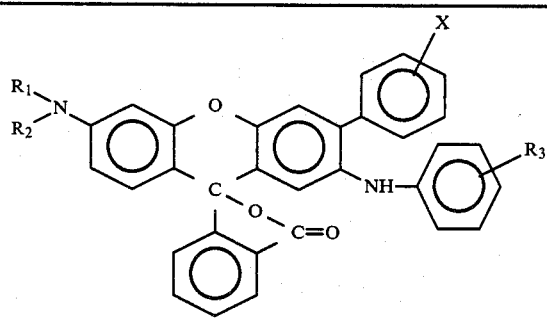

(V)

| Compound No. | $R_1$ | $R_2$ | $R_3$ | X | Color Hue |
|---|---|---|---|---|---|
| 27 | $-C_2H_5$ | $-C_2H_5$ | 2-Cl | H | Black |
| 28 | cyclohexyl | $-CH_3$ | H | H | Greenish black |
| 29 | $-C_6H_4-CH_3$ (p-tolyl) | $-C_2H_5$ | H | H | Greenish black |
| 30 | $n-C_4H_9$ | $n-C_4H_9$ | 2-Cl | H | Black |
| 31 | $-C_2H_5$ | $-C_2H_5$ | H | H | Greenish black |
| 32 | $n-C_4H_9$ | $n-C_4H_9$ | H | H | Greenish black |

| No. | R₁ | R₂ | (col) | (col) | Color Hue |
|---|---|---|---|---|---|
| 33 | cyclohexyl | —CH₃ | 2-Cl | H | Black |
| 34 | —C₂H₅ | —C₂H₅ | 4-Cl | H | Greenish black |
| 35 | 4-methylphenyl | —C₂H₅ | 4-Cl | H | Greenish black |
| 36 | —C₂H₅ | —C₂H₅ | 2-CH₃ | H | Black |
| 37 | n-C₄H₉ | n-C₄H₉ | 2-CH₃ | H | Black |
| 38 | —C₂H₅ | —C₂H₅ | 4-CH₃ | H | Greenish black |
| 39 | cyclohexyl | —CH₃ | 4-CH₃ | H | Greenish black |
| 40 | n-C₄H₉ | n-C₄H₉ | 2-F | H | Black |
| 41 | cyclohexyl | —CH₃ | 2-F | H | Black |
| 42 | —C₂H₅ | —C₂H₅ | H | 2-C₂H₅ | Greenish black |
| 43 | n-C₄H₉ | n-C₄H₉ | H | 2-C₂H₅ | Greenish black |
| 44 | —C₂H₅ | —C₂H₅ | H | 4-C₂H₅ | Greenish black |
| 45 | cyclohexyl | —CH₃ | H | 4-C₂H₅ | Greenish black |
| 46 | —C₂H₅ | i-C₅H₁₁ | H | 2-Cl | Greenish black |
| 47 | i-C₃H₇ | —CH₃ | H | 2-Cl | Greenish black |
| 48 | n-C₄H₉ | n-C₄H₉ | 4-Cl | H | Greenish black |

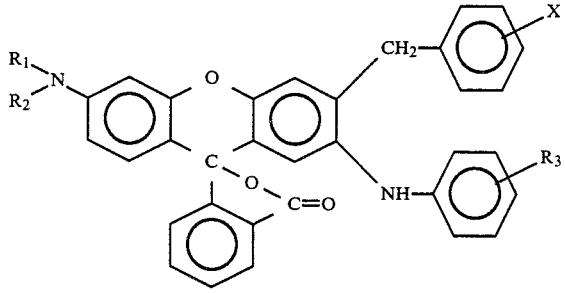

(VI)

| Compound No. | R₁ | R₂ | X | R₃ | Color Hue |
|---|---|---|---|---|---|
| 49 | —C₂H₅ | —C₂H₅ | H | H | Reddish black |
| 50 | n-C₄H₉ | n-C₄H₉ | H | H | Reddish black |
| 51 | cyclohexyl | —CH₃ | H | H | Reddish black |
| 52 | iso-C₅H₁₁ | —C₂H₅ | H | H | Reddish black |
| 53 | iso-C₅H₁₁ | iso-C₅H₁₁ | H | H | Reddish black |
| 54 | 4-methylphenyl | —C₂H₅ | H | H | Reddish black |
| 55 | —C₂H₅ | —C₂H₅ | 4-CH₃ | H | Reddish black |

TABLE-continued

| No. | R1 | R2 | X | Y | Color |
|---|---|---|---|---|---|
| 56 | —C2H5 | —C2H5 | 4-Cl | H | Reddish black |
| 57 | —C2H5 | —C2H5 | H | 2-Cl | Reddish black |
| 58 | —C2H5 | —C2H5 | H | 2-F | Reddish black |
| 59 | —C2H5 | —C2H5 | H | 2-CF3 | Reddish black |
| 60 | —C2H5 | —C2H5 | H | 2-CH3 | Reddish black |
| 61 | —C2H5 | —C2H5 | H | 4-CH3 | Reddish black |
| 62 | —C2H4—C6H5 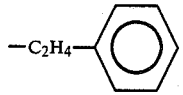 | —C2H5 | H | H | Reddish black |
| 63 | —C2H4OC2H5 | —C2H5 | H | H | Reddish black |
| 64 | —C6H11 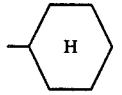 | —C6H11 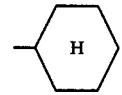 | H | H | Reddish black |
| 65 | —C3H6OC2H5 | —C2H5 | H | H | Reddish black |
| 66 | iso-C3H7 | —CH3 | H | H | Reddish black |
| 67 | n-C3H7 | —C3H7 | H | H | Reddish black |
| 68 | sec-C4H9 | sec-C4H9 | H | H | Reddish black |
| 69 | —C6H11 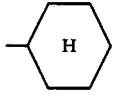 | —CH3 | 4-F | H | Reddish black |
| 70 | —C6H5 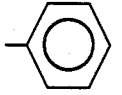 | —CH3 | H | H | Reddish black |

The heat sensitive record sheets containing the fluoran compounds of the present invention as the color formers, have excellent color-forming sensitivity, humidity decolorization resistance and oil resistance, and have a feature that the initial color density (i.e. the initial fogging) is minimum.

Now, the present invention will be described with reference to Examples. However, it should be understood that the present invention is by no means restricted by these specific Examples.

EXAMPLE 1

2-Anilino-3-ethoxyethyl-6-diethylamino-fluoran (Compound No. 1)

To 150 g of 98% sulfuric acid, 15 g of 2-(2-hydroxy-4-diethylamino)phenyl carbonyl benzoic acid was added, and completely dissolved at a temperature of from about 8° to about 14° C. Then, 10 g of 2-ethoxyethyl-4-methoxydiphenylamine was added thereto, and the mixture was reacted at a temperature of from 20° to 25° C. for 10 hours. The reaction mixture was poured into 1 liter of ice water, and then an aqueous sodium hydroxide solution was added to bring the pH to a level of at least 10. The precipitates were collected by filtration. To the cake thus obtained, 450 ml of toluene and 340 g of a 10% sodium hydroxide aqueous solution were added, and the mixture was stirred for 2 hours under reflux. Then, the toluene layer was separated by liquid separation, washed with water, and subjected to steam distillation to distill off toluene. The precipitated crystals were collected by filtration. The cake thus obtained was washed with 150 ml of methanol, and then the crystals were collected again by filtration. These crystals were dried to obtain 11 g of slightly pink 2-anilino-3-ethoxyethyl-6-diethylamino-fluoran. This fluoran compound had a melting point of from 150.5° to 152.5° C. Further, this compound had $\lambda_{max}$ at 449 nm (a molecular extinction coefficient (hereinafter referred to simply as "MEC"): $1.94 \times 10^4$) and at 595 nm (MEC: $1.73 \times 10^4$) as measured in 95% acetic acid. A solution of this product in toluene was colorless. When brought in contact with silica gel, the product readily underwent color-development and turned reddish black.

EXAMPLE 2

2-Anilino-3-ethoxyethyl-6-di-n-dibutylamino-fluoran (Compound No. 2)

To 150 g of 98% sulfuric acid, 15 g of 2-(2-hydroxy-4-di-n-butylamino)phenyl carbonyl benzoic acid was added, and completely dissolved at a temperature of from about 8° to about 14° C. Then, 10 g of 2-ethoxyethyl-4-methoxydiphenylamine was added thereto, and the mixture was reacted at a temperature of from 20° to 25° C. for 10 hours. The reaction product was treated in the same manner as in Example 1, and recrystallized from methanol to obtain 10 g of slightly pink 2-anilino-3-ethoxyethyl-6-di-n-butylamino-fluoran. This product had a melting point of from 126° to 128° C. A solution of this product in toluene was colorless. When brought in contact with silica gel, the product readily underwent color-development and turned reddish black.

EXAMPLE 3

2-(2-Chloroanilino)-3-phenyl-6-diethylamino-fluoran (Compound No. 27)

To 150 g of 98% sulfuric acid, 16.0 g of 2-(2-hydroxy-4-diethylaminobenzoyl)benzoic acid was added, and completely dissolved at a temperature of about 20° C. Then, 14.4 g of 2'-chloro-4-methoxy-2-phenyldiphenylamine was added thereto, and the mixture was reacted for 1 hour at a temperature of from 20° to 25° C. and for further 12 hours at a temperature of from 25° to 30° C. The reaction mixture was poured into 1 liter of ice water, and then an aqueous sodium hydroxide solution was added to bring the pH to a level of at least 10. The precipitates were collected by filtration. To the cake thus obtained, 450 ml of toluene and 340 g of a 10% sodium hydroxide aqueous solution were added, and the mixture was stirred for 2 hours under reflux. Then, the toluene layer was separated by liquid separation, washed with water and subjected to steam distillation to distill off toluene. The precipitated crystals were collected by filtration, and the cake thereby obtained was recrystallized from 250 ml of ethanol. The crystals were collected by filtration, and then dried to obtain 14.4 g of slightly pink 2-(2-chloroanilino)-3-phenyl-6-diethylamino-fluoran. This fluoran compound had a melting point of from 173° to 177° C. Further, this compound had $\lambda_{max}$ at 447 nm (MEC: $1.73 \times 10^4$) and at 588 nm (MEC: $2.32 \times 10^4$) as measured in 95% acetic acid. A solution of this product in toluene was colorless. When brought in contact with silica gel, the product readily underwent color-development and turned black.

EXAMPLE 4

2-Anilino-3-phenyl-6-N-cyclohexyl-N-methylamino-fluoran (Compound No. 28)

To 150 g of 95% sulfuric acid, 18.5 g of 2-(2-hydroxy-4-N-cyclohexyl-N-methyl-aminobenzoyl)benzoic acid was added, and completely dissolved at a temperature of about 20° C. Then, 13.1 g of 4-methoxy-2-phenyldiphenylamine was added thereto, and the mixture was reacted at a temperature of from 25° to 30° C. for 10 hours. The reaction product was treated in the same manner as in Example 3, and recrystallized from a solvent mixture of ethanol and toluene to obtain 17.1 g of slightly pink 2-anilino-3-phenyl-6-N-cyclohexyl-N-methylamino-fluoran. This product had a melting point of from 130° to 138° C. A solution of this product in toluene was colorless. When brought in contact with silica gel, the product readily underwent color-development and turned greenish black.

EXAMPLE 5

2-(2-Chloroanilino)-3-phenyl-6-di-n-butylamino-fluoran (Compound No. 30)

The reaction was conducted in the same manner as in Example 3 except that 19.3 g of 2-(2-hydroxy-4-dibutylaminobenzoyl)benzoic acid was used instead of 16.0 g of 2-(2-hydroxy-4-diethylaminobenzoyl)benzoic acid in Example 3, and the reaction product was recrystallized from ethanol to obtain 16.8 g of slightly pink 2-(2-chloroanilino)-3-phenyl-6-di-n-butylamino-fluoran. The product had a melting point of from 165° to 167.5° C. A solution of this product in toluene was colorless. When brought in contact with silica gel, the product readily underwent color-development and turned black.

EXAMPLE 6

2-Anilino-3-phenyl-6-diethylamino-fluoran (Compound No. 31)

The reaction was conducted in the same manner as in Example 3 except that 13.8 g of 4-methoxy-2-phenyldiphenylamine was used instead of 14.4 g of 2'-chloro-4-methoxy-2-phenyl-diphenylamine in Example 3, and the reaction product was recrystallized from ethanol to obtain 18.0 g of white 2-anilino-3-phenyl-6-diethylaminofluoran. This product had a melting point of from 153° to 159° C. A solution of this product in toluene was colorless. When brought in contact with silica gel, the product readily underwent color-development and turned greenish black.

EXAMPLE 7

2-Anilino-3-benzyl-6-diethylamino-fluoran (Compound No. 49)

To 150 g of 98% sulfuric acid, 15.0 g of 2-(2-hydroxy-4-diethylaminobenzoyl)benzoic acid was added, and completely dissolved at a temperature of about 10° C. Then, 11.6 g of 2-benzyl-4-methoxydiphenylamine was added thereto, and the mixture was reacted at a temperature of from 20° to 25° C. for 24 hours. The reaction mixture was poured into 1 liter of ice water, and an aqueous sodium hydroxide solution was added to bring the pH to a level of at least 10. The precipitates were collected by filtration. To the cake thus obtained, 450 ml of toluene and 340 g of a 10% sodium hydroxide aqueous solution were added, and the mixture was stirred for 2 hours under reflux. Then, the toluene layer was separated by liquid separation, washed with ice and subjected to steam distillation to distill off toluene. The precipitated crystals were collected by filtration. The cake thereby obtained was washed with 50 ml of methanol, and the crystals were collected again by filtration. These crystals were dried to obtain 10.2 g of white 2-anilino-3-benzyl-6-diethylamino-fluoran. This fluoran compound had a melting point of from 186° to 189° C. Further, this compound had $\lambda_{max}$ at 449 nm (MEC: $1.775 \times 10^4$) and at 591 nm (MEC: $1.788 \times 10^4$) as measured in 95% acetic acid. A solution of this product in toluene was colorless. When brought in contact with silica gel, the product readily underwent color-development and turned reddish black.

EXAMPLE 8

2-Anilino-3-benzyl-6-(N-cyclohexyl-N-methylamino)-fluoran (Compound No. 51)

To 150 g of 100% sulfuric acid, 19.1 g of 2-[2-hydroxy-4-(N-cyclohexyl-N-methylamino)benzoyl]-benzoic acid was added, and completely dissolved at a temperature of about 0° C. Then, 13.0 g of 2-benzyl-4-methoxydiphenylamine was added thereto, and the mixture was reacted at a temperature of from 0° to 2° C. for 10 hours. After the reaction, the reaction product was treated in the same manner as in Example 7, and recrystallized from ethanol to obtain 14.2 g of white 2-anilino-3-benzyl-6-(N-cyclohexyl-N-methylamino)-fluoran. This product had a melting point of from 155° to 160° C. A solution of this product in toluene was colorless. When brought in contact with silica gel, the product readily underwent color-development and turned reddish black.

EXAMPLE 9

2-Anilino-3-benzyl-6-(N-ethyl-N-isoamylamino)fluoran (Compound No. 52)

The reaction was conducted in the same manner as in Example 7 except that 19.2 g of 2-[2-hydroxy-4-(N-ethyl-N-isoamylamino)benzoyl]benzoic acid was used instead of 15.0 g of 2-(2-hydroxy-4-diethylaminobenzoyl)benzoic acid in Example 7, and the reaction product was recrystallized from ethanol to obtain 12.45 g of white 2-anilino-3-benzyl-6-(N-ethyl-N-isoamylamino)-fluoran. This product had a melting point of from 105° to 109° C. A solution of this product in toluene was colorless. When brought in contact with silica gel, the product readily underwent color-development and turned reddish black.

Now, a general process for preparing a heat sensitive record sheet using the fluoran compound of the present invention will be described.

The fluoran compound, an acidic substance and, if necessary, a heat-melting substance (which is used when the fluoran compound or the acidic substance does not melt at the desired temperature) are finely pulverized and mixed with a binder solution or dispersion which has been prepared by dissolving or dispersing a binder in a solvent or dispersing medium. The coating mixture thereby obtained is applied onto a support such as a sheet of paper, a plastic sheet or a resin-coated paper sheet, and then dried to obtain a heat sensitive record sheet. For the preparation of the coating mixture, the components may be pulverized independently or in a proper combination prior to mixing together, or all together after they are put together.

The coating mixture preferably comprises 1 part by weight of the fluoran compound, from 2 to 10 parts by weight of the acidic substance, from 0 to 10 parts by weight of the heat-melting substance, from 2 to 10 parts by weight of the binder, and from 50 to 150 parts by weight of the solvent or dispersing medium.

The solvent or dispersing medium is preferably the one which does not substantially dissolve the fluoran compound and the acidic substance. As such a solvent or dispersing medium, water is most preferred, and a hydrocarbon such as hexane or ligroin is also useful. As the binder to be used in the present invention, there may be mentioned polyvinyl alcohol, hydroxyethyl cellulose, polvinyl pyrrolidone or a copolymer of styrene-maleic anhydride.

As the heat-melting substance, there may be used stearic acid amide, oleic acid amide, ethylene-bis-stearoamide, benzenesulfoanilide or benzyloxyacetanilide.

The acidic substance useful in the present invention is the one which is capable of developping a color when brought in contact with the above fluoran compound. Specifically, there may be mentioned known compounds such as 4-t-butylphenol, 4-phenylphenol, methyl-4-hydroxy benzoate, 4,4'-isopropylidene diphenol, 4,4'-isopropylidene(2,6-dibromophenol), bis(4-hydroxyphenyl)sulfone, benzyl p-hydroxy benzoate, sec-butyl p-hydroxy benzoate, and 3-($\alpha$-methylbenzyl)salicylic acid. These acidic substances may be used alone or in combination as a mixture of two or more different kinds.

Further, various assisting agents may be added to the coating solution. For instance, there may be mentioned a dispersant such as sodium dioctylsulfosuccinate or sodium dodecylbenzene sulfonate, an ultraviolet absorber such as a benzophenone type or a triazole type, other defoaming agents, fluorescent dyestuffs or coloring dyestuffs.

As the support, there may be employed papers, plastic films, synthetic papers or fabric sheets. Particularly preferred is a paper. The amount of the coating solution to be applied onto the support is not critical, but is usually within a range of from 2 to 15 g/m$^2$, preferably from 3 to 10 g/m$^2$.

Now, the heat sensitive record sheets wherein the fluoran compounds of the present invention are used, will be described with reference to Application Examples.

The properties of the heat sensitive record sheets were determined by the following test methods. Namely, the color densities such as the initial color densities, the decolorization densities of the color formers left in a humidified atmosphere after the heat color-development at various temperatures (i.e. the humidity decolorization resistance) or the decolorization densities when brought in contact with castor oil (i.e. the oil resistance), were measured by means of Macbeth RD-514 model reflective density meter. The heat color-development was conducted at a heating temperature of from 60° to 170° C. for a heating time of 3 seconds under a load of 100 g/cm$^2$ by means of Iodiaceta model thermotest rhdiacita (manufactured by French National Fiber Research Institute). Further, the decolorization of the color formers after the heat color development was conducted in a constant temperature and humidity testing apparatus.

Application Example 1

Mixtures having the following compositions were separately pulverized for 3 hours by means of a paint conditioner (Red Devil, tradename) to obtain Dispersions A, B and C.

|  | Parts by weight |
| --- | --- |
| Dispersion A | |
| 2-Anilino-3-ethoxyethyl-6-diethylamino fluoran (Compound No. 1) | 4 |
| 10% Polyvinyl alcohol aqueous solution | 34 |
| 5% Defoaming agent (San nopco 1407, manufactured by Sannopco Co.) | 2 |
| Dispersion B | |
| Bisphenol A | 6 |
| 10% Polyvinyl alcohol aqueous solution | 20 |
| Water | 14 |
| Dispersion C | |
| Aluminum hydroxide | 10 |
| 10% Polyvinyl alcohol aqueous solution | 20 |
| Water | 10 |

Dispersions A, B and C, and water were mixed in a weight ratio of 3:9:5:3 to obtain a coating composition for a heat sensitive record sheet. This coating composition was coated on the surface of a sheet of high quality paper by means of a wire bar coater in such an amount that the weight of the solid after drying would become 5 g/m$^2$, and then dried in an air-circulating dryer at room temperature to obtain a heat sensitive record sheet (a) of the present invention.

COMPARATIVE EXAMPLE 1

In the same manner as in Example 1 except that Dispersion D was used instead of Dispersion A, a comparative heat sensitive record sheet (ag) was prepared.

| Dispersion D | Parts by weight |
| --- | --- |
| 2-Anilino-3-methyl-6-diethylamino fluoran | 4 |
| 10% Polyvinyl alcohol aqueous solution | 34 |
| 5% Defoaming agent (San nopco 1407) | 2 |

The heat sensitive record sheet of the present invention and the comparative heat sensitive record sheet thus obtained, were tested for their color-forming sensitivity, humidity decolorization resistance, oil resistance and initial color density. The results are shown in Table 1.

Application Example 2

Heat sensitive record sheets (b) to (i) were prepared in the same manner as in Application Example 1 except that fluoran compounds as identified in Table 1 were used instead of Compound No. 1 used in Application Example 1. These heat sensitive record sheets of the present invention were tested for their properties in the same manner as in Application Example 1. The results are shown in Table 1.

resistance and had a feature that the initial fogging was minimum. Particularly, they were superior to the comparative heat sensitive record sheet in the color-forming sensitivity, humidity decolorization resistance and oil resistance, and practically adequately qualified as heat sensitive record sheets for various fields of recording, particularly for high speed recording or POINT OF SALES POS.

Application Example 3

Mixtures having the following compositions were separately pulverized for 3 hours by means of a paint conditioner (Red Devil, tradename) to obtain Dispersions E, B and C.

TABLE 1

| | Heat sensitive record sheet No. | Fluoran compounds of the formula (IV) | | | | n | *1 Initial color density | *2 Color-forming sensitivity | *3 Humidity de-colorization resistance | *4 Oil resistance |
|---|---|---|---|---|---|---|---|---|---|---|
| | | $R_1$ | $R_2$ | $R_3$ | $R_4$ | | | | | |
| Application Example 1 | (a) | $-C_2H_5$ | $-C_2H_5$ | H | $-C_2H_5$ | 2 | 0.11 | 107 | 102 | 45 |
| Application Example 2 | (b) | $-n-C_4H_9$ | $-n-C_4H_9$ | H | $-C_2H_5$ | 2 | 0.10 | 108 | 104 | 55 |
| Application Example 2 | (c) | $-\langle H \rangle$ (cyclohexyl) | $CH_3$ | H | $-C_2H_5$ | 2 | 0.12 | 110 | 106 | 45 |
| Application Example 2 | (d) | $-C_2H_5$ | $-C_2H_5$ | H | $-C_2H_5$ | 1 | 0.11 | 112 | 100 | 40 |
| Application Example 2 | (e) | $-C_4H_9$ | $-C_4H_9$ | H | $-C_2H_5$ | 1 | 0.13 | 113 | 102 | 47 |
| Application Example 2 | (f) | $-\langle H \rangle$ (cyclohexyl) | $-CH_3$ | H | $-i-C_3H_7$ | 1 | 0.15 | 112 | 98 | 50 |
| Application Example 2 | (g) | $-CH_2-\langle \bigcirc \rangle$ (benzyl) | $-CH_3$ | H | $-C_8H_{17}$ | 2 | 0.08 | 106 | 103 | 52 |
| Application Example 2 | (h) | $-\langle \bigcirc \rangle$ (phenyl) | $-i-C_3H_7$ | o-Cl | $-C_4H_9$ | 3 | 0.14 | 107 | 106 | 45 |
| Application Example 2 | (i) | $-\langle H \rangle$ (cyclohexyl) | H | o-F | $-\langle H \rangle$ (cyclohexyl) | 4 | 0.10 | 108 | 104 | 51 |
| Comparative Example 1 | (ag) | 2-Anilino-3-methyl-6-diethylamino fluoran | | | | | 0.27 | 118 | 94 | 39 |

Notes:
*1: Color density of the white color portion of the heat sensitive color-forming layer in a non-developed state.
*2: Heating temperature required to obtain a developed color density of 1.0. The lower the temperature, the better the color-forming sensitivity.
*3: Humidity decolorization resistance after the color development by heating. The portion having a developed color density of 1.0 was kept in an atmosphere of 50° C. under a relative humidity of 90% for 24 hours. Then, the color density ($D_1$) of the developed portion was measured. Thus the color former-remaining rate (%) = ($D_1$/1.00 × 100) was obtained and taken as the humidity decolorization resistance.
*4: A 5% chloroform solution of castor oil was coated on a polyester film by means of a film applicator (20 μm scale) and dried in air. Then, the castor oil on the film was stamped by means of a rubber stamp of 1.5 × 1 cm onto a portion having a developed color density of 1.0. The portion was treated at 50° C. under a relative humidity of 90% for 3 hours in a constant temperature and humidity testing apparatus. Then the color density ($D_2$) was measured. Thus the color former-remaining rate (%) = ($D_2$/1.00 × 100) was obtained and taken as the oil resistance.

As is apparent from Table 1, the heat sensitive record sheets wherein the fluoran compounds of the present invention were used, exhibited excellent color-forming sensitivity, humidity decolorization resistance and oil

| | Parts by weight |
|---|---|
| Dispersion E | |
| 2-(2-Chloroanilino)-3-phenyl- | 4 |

-continued

| | Parts by weight |
|---|---|
| diethylamino fluoran (Compound No. 27) | |
| 10% Polyvinyl alcohol aqueous solution | 34 |
| 5% Defoaming agent (San nopco 1407, manufactured by Sannopco Co.) | 2 |
| Dispersion B | |
| Bisphenol A | 6 |
| 10% Polyvinyl alcohol aqueous solution | 20 |
| Water | 14 |
| Dispersion C | |
| Aluminum hydroxide | 10 |
| 10% Polyvinyl alcohol aqueous solution | 20 |
| Water | 10 |

Dispersions E, B and C, and water were mixed in a weight ratio of 3:9:5:3 to obtain a coating composition for a heat sensitive record sheet. This coating composition was coated on the surface of high quality paper by means of a wire bar coater in such an amount that the weight of the solid component after drying would become 5 g/m², and then dried in an air-circulating dryer at room temperature to obtain a heat sensitive record sheet (j).

A comparative heat sensitive record sheet (ag) was prepared in the same manner as in Application Example 3 except that Dispersion D as used in Comparative Example 1 was employed instead of Dispersion E.

The heat sensitive record sheet of the present invention and the comparative heat sensitive record sheet thus obtained, were tested for their color-forming sensitivity, humidity decolorization resistance, oil resistance and initial color density. The results are shown in Table 2.

Application Example 4

Heat sensitive record sheets (k) to (v) were prepared in the same manner as in Application Example 3 except that fluoran compounds as identified in Table 2 were used instead of Compound No. 27 used in Application Example 3. These heat sensitive record sheets of the present invention were tested for their properties in the same manner as in Application Example 3. The results are shown in Table 2.

TABLE 2

| | Heat sensitive record sheet No. | Fluoran compounds of the formula (V) | | | | *1 Initial color density | *2 Color-forming sensitivity | *3 Humidity decolorization resistance | *4 Oil resistance |
|---|---|---|---|---|---|---|---|---|---|
| | | $R_1$ | $R_2$ | X | $R_3$ | | | | |
| Application Example 3 | (j) | —$C_2H_5$ | —$C_2H_5$ | H | 2-Cl | 0.12 | 108 | 91 | 48 |
| Application Example 4 | (k) | —$C_2H_5$ | —$C_2H_5$ | H | H | 0.14 | 113 | 95 | 43 |
| Application Example 4 | (l) | n-$C_4H_9$ | n-$C_4H_9$ | H | 2-Cl | 0.08 | 114 | 65 | 35 |
| Application Example 4 | (m) | n-$C_4H_9$ | n-$C_4H_9$ | H | H | 0.11 | 117 | 96 | 44 |
| Application Example 4 | (n) | phenyl | —$CH_3$ | H | H | 0.14 | 110 | 98 | 60 |
| Application Example 4 | (o) | —$C_2H_5$ | —$C_2H_5$ | H | 4-Cl | 0.15 | 115 | 75 | 50 |
| Application Example 4 | (p) | —$C_2H_5$ | —$C_2H_5$ | H | 2-$CH_3$ | 0.19 | 117 | 86 | 49 |
| Application Example 4 | (q) | phenyl | —$CH_3$ | H | 2-$CH_3$ | 0.12 | 108 | 67 | 55 |
| Application Example 4 | (r) | n-$C_4H_9$ | n-$C_4H_9$ | H | 4-$CH_3$ | 0.11 | 115 | 90 | 45 |
| Application Example 4 | (s) | —$C_2H_5$ | —$C_2H_5$ | H | 2-F | 0.13 | 109 | 93 | 64 |
| Application Example 4 | (t) | n-$C_4H_9$ | n-$C_4H_9$ | H | 2-F | 0.17 | 108 | 80 | 38 |
| Application Example 4 | (u) | —$C_2H_5$ | —$C_2H_5$ | 4-$C_2H_5$ | H | 0.12 | 114 | 78 | 57 |
| Application Example 4 | (v) | n-$C_4H_9$ | n-$C_4H_9$ | 4-$C_2H_5$ | H | 0.13 | 118 | 69 | 41 |
| Comparative Example 1 | (ag) | 2-Anilino-3-methyl-6-diethylamino fluoran | | | | 0.27 | 118 | 94 | 39 |

In Table 2, *1 to *4 have the same meanings as in Table 1.

As is apparent from Table 2, the heat sensitive recording sheets wherein the fluoran compounds of the present invention were used, exhibited excellent humidity decolorization resistance and oil resistance, and had a minimum initial color density.

Particularly, they were superior to the comparative heat sensitive record sheet in their color-forming sensitivity, and adequately qualified as heat sensitive record sheets for various fields of recording, particularly for high speed recording or POS.

Application Example 5

Mixtures having the following compositions were separately pulverized for 3 hours by means of a paint conditioner (Red Devil, tradename) to obtain Dispersions F, B and C.

|  | Parts by weight |
|---|---|
| Dispersion F | |
| 2-Anilino-3-benzyl-6-diethylamino fluoran (Compound No. 49) | 4 |
| 10% Polyvinyl alcohol aqueous solution | 34 |
| 5% Defoaming agent (San nopco 1407) | 2 |
| Dispersion B | |
| Bisphenol A | 6 |
| 10% Polyvinyl alcohol aqueous solution | 20 |
| Water | 14 |
| Dispersion C | |
| Aluminum hydroxide | 10 |
| 10% Polyvinyl alcohol aqueous solution | 20 |
| Water | 10 |

Dispersions F, B and C, and water were mixed in a weight ratio of 3:9:5:3 to obtain a coating composition for a heat sensitive record sheet. This coating composition was coated on the surface of high quality paper by means of a wire bar coater in such an amount that the weight of the solid component after drying would become 5 g/m², and dried in an air-circulating dryer at room temperature to obtain a heat sensitive record sheet (w) of the present invention.

A comparative heat sensitive record sheet (ag) was prepared in the same manner as in Application Example 5 except that Dispersion D as used in Comparative Example 1 was employed instead of Dispersion F in Application Example 5.

The heat sensitive record sheet of the present invention and the comparative heat sensitive record sheet thus obtained, were tested for their color-forming sensitivity and initial color density. The results are shown in Table 3.

Application Example 6

Heat sensitive record sheets (x) to (af) were prepared in the same manner as in Application Example 5 except that fluoran compounds as identified in Table 3 were used instead of Compound No. 49 used in Application Example 5. These heat sensitive record sheets of the present invention were tested for their properties in the same manner as in Application Example 5. The results are shown in Table 3.

TABLE 3

| | Heat sensitive color sheet No. | Fluoran compounds of the formula (VI) | | | | *1 Initial color density | *2 Color-forming sensitivity |
|---|---|---|---|---|---|---|---|
| | | $R_1$ | $R_2$ | X | $R_3$ | | |
| Application Example 5 | (w) | $-C_2H_5$ | $-C_2H_5$ | H | H | 0.14 | 102 |
| Application Example 6 | (x) | n-$C_4H_9$ | n-$C_4H_9$ | H | H | 0.15 | 104.5 |
| Application Example 6 | (y) | cyclohexyl | $CH_3$ | H | H | 0.17 | 109 |
| Application Example 6 | (z) | iso-$C_5H_{11}$ | $-C_2H_5$ | H | H | 0.15 | 107 |
| Application Example 6 | (aa) | iso-$C_5H_{11}$ | iso-$C_5H_{11}$ | H | H | 0.14 | 101.5 |
| Application Example 6 | (ab) | 4-methylphenyl | $-C_2H_5$ | H | H | 0.12 | 112 |
| Application Example 6 | (ac) | $-C_2H_5$ | $-C_2H_5$ | p-$CH_3$ | H | 0.16 | 96 |
| Application Example 6 | (ad) | $-C_2H_5$ | $-C_2H_5$ | p-Cl | H | 0.12 | 98 |
| Application Example 6 | (ae) | $-C_2H_5$ | $-C_2H_5$ | H | 2-Cl | 0.14 | 104 |
| Application Example 6 | (af) | $-C_2H_5$ | $-C_2H_5$ | H | 2-F | 0.15 | 103 |
| Comparative Example 1 | (ag) | 2-Anilino-3-methyl-6-diethylamino fluoran | | | | 0.27 | 118 |

In Table 3, *1 and *2 have the same meanings as in Table 1.

It is evident from Table 3, the heat sensitive record sheets wherein the fluoran compounds of the present invention were used, exhibited excellent color-forming sensitivity and had a minimum initial color density. Thus, they are superior to the comparative heat sensitive record sheet, particularly in the color-forming sensitivity, and adequately qualified as heat sensitive record sheets for various fields of recording, particularly for high speed recording.

We claim:
1. A fluoran compound having the formula:

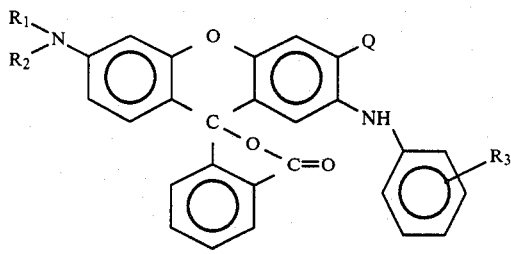 (I)

wherein each of R₁ and R₂ is a hydrogen atom, a straight chain or branched alkyl group having from 1 to 8 carbon atoms, a cyclohexyl group, a substituted or unsubstituted phenyl group, or a substituted or unsubstituted benzyl group, Q is either

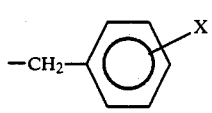

wherein X is a hydrogen atom, a halogen atom, or a straight chain or branched alkyl group having from 1 to 8 carbon atoms,

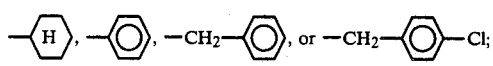

wherein X is as defined above, or —(CH₂)ₙOR₄ wherein R₄ is a straight chain or branched alkyl group having from 1 to 8 carbon atoms, a cycloalkyl group, a substituted or unsubstituted phenyl group, or a substituted or unsubstituted benzyl group, and n is an integer of from 1 to 8, and R₃ is a hydrogen atom, a halogen atom, a lower fluoroalkyl group, an acyl group, an alkoxy group, an alkoxyalkyl group, or a straight chain or branched alkyl group having from 1 to 8 carbon atoms.

2. The fluoran compound according to claim 1, wherein R₁ is —C₂H₅, —C₄H₉, —C₆H₁₃, —C₈H₁₇,

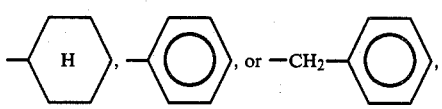

R₂ is —CH₃, —C₂H₅, —C₄H₉, —CH(CH₃)₂, or i-C₅H₁₁; R₃ is —H, 2-Cl, 2-F, 4-CH₂OC₂H₅, 4-CH₃, or 2-CF₃; and Q is —(CH₂)ₙOR₄ wherein R₄ is —CH₃, —C₂H₅, n-C₃H₇, —C₄H₉, —CH(CH₃)₂, —C₈H₁₇,

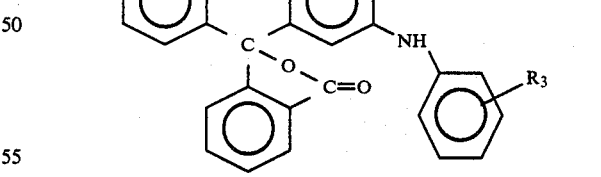

and n is 1, 2, 3 or 4.

3. The fluoran compound according to claim 1, wherein R₁ is —C₂H₅, i-C₃H₇, n-C₄H₉,

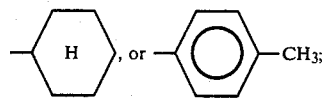

R₂ is —CH₃, —C₂H₅, n-C₄H₉, or i-C₅H₁₁; R₃ is —H, 2-Cl, 4-Cl, 2-CH₃, 4-CH₃, or 2-F; and Q is

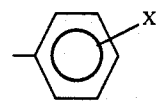

wherein X is —H, 2-C₂H₅, 4-C₂H₅, or 2-Cl.

4. The fluoran compound according to claim 1, wherein R₁ is —C₂H₅, n-C₃H₇, i-C₃H₇, n-C₄H₉, sec-C₄H₉, i-C₅H₁₁,

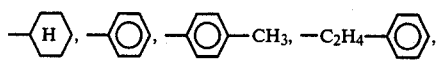

—C₂H₄OC₂H₅, or —C₃H₆OC₂H₅; R₂ is —CH₃, —C₃H₇, n-C₄H₉, sec-C₄H₉, i-C₅H₁₁, or

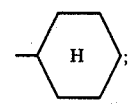

R₃ is —H, 2-Cl, 2-F, 2-CH₃, or 4-CH₃; Q is

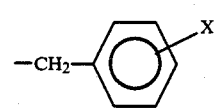

wherein X is —H, 4-CH₃, 4-Cl, or 4-F.

5. A heat sensitive record sheet which comprises a coated layer comprising a fluoran compound having the formula:

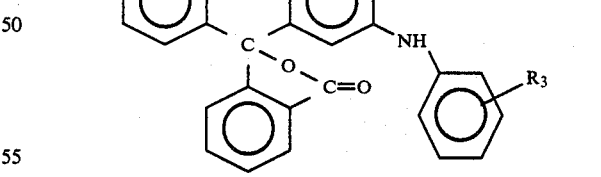 (I)

wherein each of R₁ and R₂ is a hydrogen atom, a straight chain or branched alkyl group having from 1 to 8 carbon atoms, a cyclohexyl group, a substituted or unsubstituted phenyl group, or a substituted or unsubstituted benzyl group, Q is

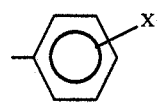

wherein X is a hydrogen atom, a halogen atom, or a straight chain or branched alkyl group having from 1 to 8 carbon atoms,

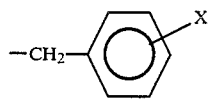

wherein X is as defined above, or $-(CH_2)_nOR_4$ wherein $R_4$ is a straight chain or branched alkyl group having from 1 to 8 carbon atoms, a cycloalkyl group, a substituted or unsubstituted phenyl group, or a substituted or unsubstituted benzyl group, and n is an integer of from 1 to 8, and $R_3$ is a hydrogen atom, a halogen atom, a lower fluoroalkyl group, an acyl group, an alkoxy group, an alkoxyalkyl group, or a straight chain or branched alkyl group having from 1 to 8 carbon atoms.

* * * * *